(12) United States Patent
Schreiber et al.

(10) Patent No.: US 7,452,364 B2
(45) Date of Patent: Nov. 18, 2008

(54) SURGICAL MARKER/CONNECTOR

(76) Inventors: Helmut Schreiber, 19701 Shaker Blvd., Shaker Heights, OH (US) 44122; Albert N. Santilli, 28326 Gates Mills Blvd., Pepper Pike, OH (US) 44124

( * ) Notice: Subject to any disclaimer, the term of this patent is extended or adjusted under 35 U.S.C. 154(b) by 0 days.

(21) Appl. No.: 11/112,292

(22) Filed: Apr. 22, 2005

(65) Prior Publication Data
US 2006/0253153 A1 Nov. 9, 2006

(51) Int. Cl.
*A61B 17/08* (2006.01)
(52) U.S. Cl. .................. 606/153; 606/155; 600/420
(58) Field of Classification Search .............. 606/233, 606/116, 148, 232, 69, 155, 153, 151; 600/420, 600/421, 426, 431; 604/116, 93.01
See application file for complete search history.

(56) References Cited

U.S. PATENT DOCUMENTS

| | | | |
|---|---|---|---|
| 4,041,931 A * | 8/1977 | Elliott et al. ............... 128/899 |
| 4,592,356 A | 6/1986 | Gutierrez |
| 5,059,197 A | 10/1991 | Urie et al. |
| 5,158,084 A | 10/1992 | Ghiatas |
| 5,197,482 A | 3/1993 | Rank et al. |
| 5,221,269 A | 6/1993 | Miller et al. |
| 5,409,004 A | 4/1995 | Sloan |
| 5,578,036 A * | 11/1996 | Stone et al. ............... 606/69 |
| 5,709,697 A | 1/1998 | Ratcliff et al. |
| 5,989,265 A | 11/1999 | Bouquet De La Joliniere et al. |
| 6,093,201 A * | 7/2000 | Cooper et al. ............... 606/232 |
| 6,187,020 B1 * | 2/2001 | Zegdi et al. ............... 606/153 |
| 6,235,054 B1 * | 5/2001 | Berg et al. ............... 623/1.36 |
| 6,356,782 B1 | 3/2002 | Sirimanne et al. |
| 6,405,733 B1 | 6/2002 | Fogarty et al. |
| 6,558,400 B2 | 5/2003 | Deem et al. |
| 2004/0002721 A1 * | 1/2004 | Podmore et al. ............ 606/155 |
| 2004/0024386 A1 | 2/2004 | Deem et al. |

OTHER PUBLICATIONS

Helmut Schreiber, M.D., Indukumar Sonpal, M.D. and Linda Petterson, M.D.—The Routine Use of a Gastropexy with a Radiologic Maker Without a Gastrostomy after Roux-en-y Gastric Bypass, Obesity Surgery 12, 2002.

The Cleveland Center for Bariatric Surgery (CCBS)—St. Vincent Charity Hospital—The CCBS Open Gastric Bypass, 2004.

Mathias A.L. Fobi, M.D., Kathleen Chicola, M.D., Hoil Lee, M.D. 2—Access to the Bypassed Stomach After Gastric Bypass, Mar. 17, 1988.

(Continued)

*Primary Examiner*—Nicholas D Lucchesi
*Assistant Examiner*—Christopher D Koharski
(74) *Attorney, Agent, or Firm*—Wayne D. Porter, Jr.

(57) ABSTRACT

A surgical marker/connector in the form of a ring includes a plurality of small suture attachments that are disposed about the ring. The suture attachments preferably are in the form of loops that lie in a plane that includes the ring itself. The loops are large enough to receive sutures which, in turn, can be used to connect the ring to a portion of a patient's body, or to connect separate portions of a patient's body to each other using the marker/connector as an intermediate connector. At least a portion of the marker/connector is made of a material that can be observed by fluoroscopic examination.

12 Claims, 3 Drawing Sheets

OTHER PUBLICATIONS

Mathias A.L. Fobi, M.D., Hoil Lee, M.D.1—The Surgical Technique of the Fobi-Pouch Operation for Obesity (The Transected Silastic Vertical Gastric Bypass)—Obesity Surgery, 8, 1998.

Johnson & Johnson Gateway—The Mammotome Breast Biopsy System, Internet advertisement, Jul. 2004.

GI Supply—GI Spot—www/gis-spot.com/index.html, Internet advertisement, Jul. 2004.

Baritec, Inc., GaBP Ring Autolock System, brochure, El Dorado Hills, California.

Baritec, Inc., GaBP Ring Autolock System, brochure, El Dorado Hills, California, publication date unknown.

* cited by examiner

SURGICAL MARKER/CONNECTOR

BACKGROUND OF THE INVENTION

1. Field of the Invention

The invention relates to surgical procedures and, more particularly, to an implantable device that can be used as a fluoroscopic marker or as a fluoroscopic marker/tissue connector. As used herein, the phrase "marker/connector" or "surgical marker/connectors" also shall mean "implant and marker/connector" or "surgical implant and marker/connector," respectively.

2. Description of the Prior Art

While the present invention has application in various types of surgical procedures, it will be described in the context of gastric bypass surgery as used for the treatment of obesity. The most common gastric bypass procedure performed today is known as the Roux-en-Y gastric bypass procedure (RYGB). In the RYGB procedure, a six-inch to eight-inch incision is made that extends from the end of the sternum to just above the navel. The stomach is completely divided into two unequal portions—a small upper pouch and a large lower gastric pouch (excluded stomach). The upper pouch typically measures less than about one ounce, preferably about one-half ounce, or 15 cc, while the excluded stomach remains generally intact and continues to secrete stomach juices that flow through the intestinal tract.

The small intestine is severed at a location distal of the duodenum or proximal of the jejunum. The severed end of the small intestine then is brought from the lower abdomen, behind the colon and the bypassed stomach, and joined with the upper pouch to form an end-to-end anastomosis created through a half-inch opening, also called the stoma. This rerouted segment of the small intestine is called the "Roux loop" and carries food from the upper pouch to the remainder of the intestines where the food is digested. The severed end of the segment of the duodenum that is part the excluded stomach is connected to the Roux loop by means of an anastomotic connection. The connection is located approximately 100 cm from the stoma, and typically is made by using a stapling instrument. Prior to completion of the surgical procedure, a gastropexy commonly is performed to attach the excluded stomach to the abdominal wall or to the diaphragm, primarily to prevent the excluded stomach from being displaced within the abdominal cavity.

The RYGB procedure described permits digestive juices from the bypassed stomach, pancreas and liver to join the food stream from the small upper pouch and Roux loop to begin digesting the food. The remainder of the intestinal tract is not disturbed. Due to the small size of the upper pouch, patients are forced to eat at a slower rate and are satiated much more quickly, thereby reducing their caloric intake. Moreover, because the food enters the intestines directly, certain undesirable foods such as sweets create unpleasant feelings of nausea, diarrhea, nervousness, and sweating, which in turn discourages patients from developing or maintaining unhealthy eating habits. The RYGB procedure typically demonstrates a loss of at least 50% of excess body weight; approximately 60% of the patients will be able to maintain this weight loss for at least five years.

In certain cases it is necessary to perform post-operative surgical procedures. For example, some patients require that the excluded stomach be decompressed post-operatively. In order to accommodate this possibility, it has been known to insert a gastrostomy tube through the abdominal wall and into the excluded stomach and leave it there for several days until the need for decompression passes. In such cases, the gastrostomy tube has been provided with a silastic ring having a metal marker. The metal marker permits the excluded stomach to be quickly and accurately located in the abdominal cavity by fluoroscopic examination. While the practice of inserting a gastrostomy tube is effective to avoid the need for post-operative decompression, it also is an unnecessary procedure for many patients. Experience with patients that have not been fitted with a gastrostomy tube at the time of surgery shows that decompression is needed only in about one out of every 50-75 patients.

A problem in performing decompression in patients that have not had a gastrostomy tube inserted at the time of surgery is that the large pouch cannot be located accurately and, once located, cannot be held in a stable position for purposes of inserting an endoscope or trochar/cannula. In order to deal with such problems, it has been known to perform the gastropexy by using a circular wire suture having a diameter of approximately one inch. Because the suture is made of metal, it serves as a marker for fluoroscopic location of the bypassed stomach. The suture also assists in stabilizing the excluded stomach for post-operative insertion of an endoscope or a trochar/cannula.

The use of markers to subsequently locate areas of surgical interest is well known, particularly in the field of breast biopsies. See, for example, U.S. Pat. Nos. 4,592,356; 5,059,197; 5,158,084; 5,197,482; 5,221,269; 5,409,004; 5,709,697; 5,989,265; 6,356,782 and 6,405,733. In general, these patents disclose the concept of using metallic tissue markers that are implanted or otherwise attached to an internal portion of a patient's body. FIGS. 2B and 2C of the '782 patent disclose ring-like markers, while the '269 patent discloses a helical wire marker. Many of the patents in question disclose barbs of various types to retain the marker in place.

A problem with prior markers is that they have been difficult to use and install. In particular, such markers have not facilitated the attachment of the marker to the portion of the body to be marked. Moreover, such markers have not facilitated the attachment of one portion of the body to another. Although the use of hooks or barbs makes the implantation of a marker easier to perform, such hooks or barbs are generally undesirable for purposes of long-term retention of the marker. The use of a wire suture, while effective as a marker and connector, generally is undesirable because it can be difficult to install. Moreover, a wire suture also may not provide an effective technique to hold tissue in place for purposes of inserting objects such as an endoscope or a trochar.

Desirably, a surgical marker/connector would be available that would be easy to use and install, and which would permit portions of the body that need to be connected to each other to be connected in a convenient and secure manner. Preferably the marker/connector would be made of a material that would facilitate location by fluoroscopic techniques. In the particular case of a gastroplexy performed as part of the RYGB procedure, the marker/connector preferably would permit an endoscope or a trochar/cannula to be inserted quickly and accurately.

SUMMARY OF THE INVENTION

In response to the foregoing concerns, the present invention provides a new and improved surgical marker/connector. The marker/connector according to the invention is in the form of a ring. In the preferred embodiment, the ring is circular and a plurality of suture attachments in the form of small loops are disposed about the periphery of the ring. The loops preferably lie in a plane that includes the ring itself. The loops are large enough to receive sutures which, in turn, can be used to connect the marker/connector to a portion of a patient's body, or to connect separate portions of a patient's body to each other using the marker/connector as an intermediate connector. For example, in the RYGB procedure, the marker/connector could be sewn to a portion of a patient's excluded stomach for which marking is desired, or it could be used as an intermediate connection between a desired portion of the patient's excluded stomach and another portion of the patient's body, such as the abdominal wall. In order to serve as a fluroscopic marker/connector, at least a portion of the marker/connector is made of a metal such as stainless steel, titanium, or alloys thereof.

The marker/connector according to the invention is easy to use due to the convenience in suturing afforded by the suture attachments. Because the marker/connector is made partially or entirely of metal, it can serve as an effective fluoroscopic marker. In the particular case of the RYGB procedure, because the ring is securely attached to the excluded stomach and to the abdominal wall or to the diaphragm, the ring can be a target through which an endoscope or a trochar/cannula can be inserted. The ring prevents the excluded stomach from moving as the endoscope or trochar is inserted, thereby greatly facilitating the procedure.

The foregoing and other features and advantages of the invention will be apparent from a review of the following description of the invention, taken together with the attached drawings.

DESCRIPTION OF THE PREFERRED EMBODIMENT

Figure 1:
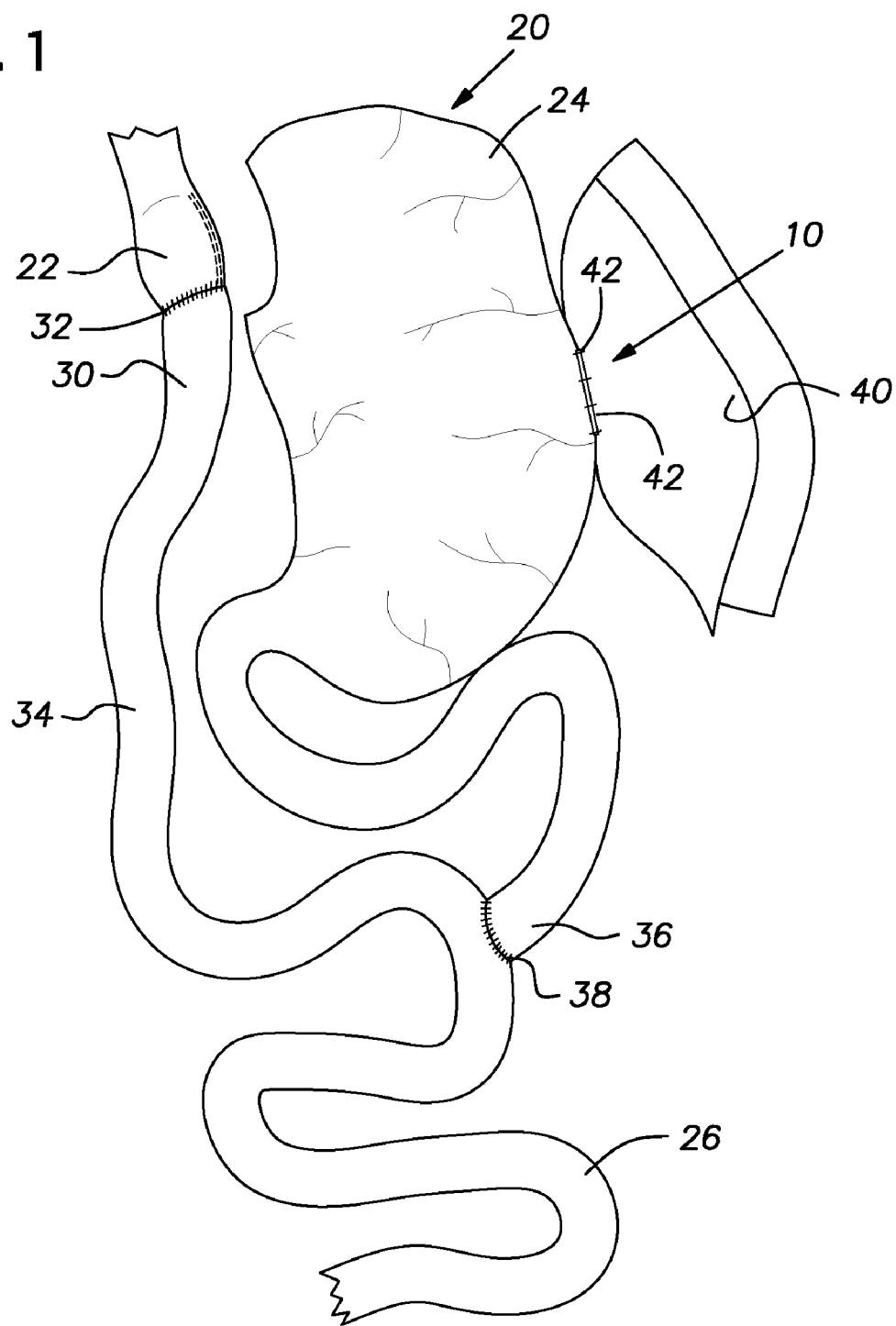
FIG. 1 is a schematic view of a patient's stomach and small intestine after undergoing the RYGB procedure in which a surgical marker/connector according to the invention has been employed.
Figures 2, 3:
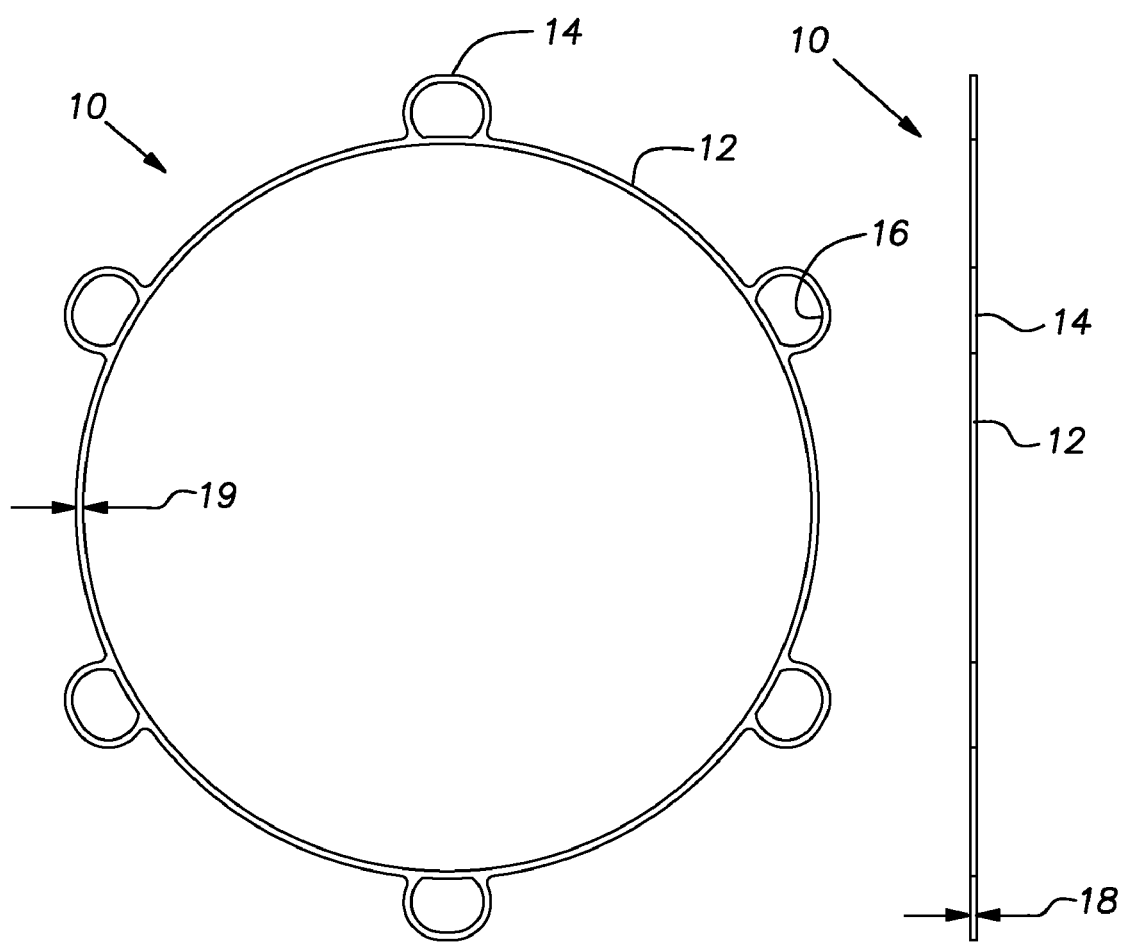
FIG. 2 is a top plan view of a surgical marker/connector according to the invention.
FIG. 3 is a side elevation view of the surgical marker/connector of FIG. 2.

Referring to FIGS. 1-3, a surgical marker/connector according to the invention is indicated generally by the reference numeral 10. As shown in FIGS. 2 and 3, the marker/connector 10 includes a closed circular ring 12 of fixed dimensions having an inner diameter and an outer diameter from which a plurality of small loops or suture attachments 14 project and are disposed equidistantly about the periphery thereof. The ring 12 is approximately one inch in diameter. The loops 14 are generally elliptical in shape, being defined by circular inner side portions 16 approximately 0.0413 inch in diameter, whose centers are separated by approximately 0.0075 inch. As can be seen in FIG. 3, the ring 12 and the loops 14 lie in a common plane. The area of the opening defined by each of the loops 14 is substantially smaller than the area of the opening defined by the inner diameter of the ring 12.

It is expected that the marker/connector 10 can be made of any material suitable for use in the human body and which will perform a fluoroscopic marking function and a mechanical connector function. The marker/connector 10 can be made in any type of manufacturing operation. Preferably the entire marker/connector 10 is made of metal such as stainless steel, titanium, or alloys thereof in a stamping or laser cutting operation, although only portions of the marker/connector 10 need to be made of metal provided the remainder is strong enough to perform a mechanical connector function.

The marker/connector 10 can be made in any desired thickness, as indicated by the reference numeral 18 in FIG. 3, although a thickness of about 0.0085 inch is preferred. The width of the ring 12 and the loops 14, as indicated by the reference numeral 19 in FIG. 2, is about 0.010 inch. The size and shape of the ring 12, the size and shape of the loops 14, and the relative sizes thereof can be chosen to fit the surgical procedure at hand. As a general design constraint, however, the ring 12 should be large enough to be an effective fluoroscopic marker/connector, an effective tissue connector, and a target for an endoscope or a trochar. The loops 14 should be large enough to enable the surgeon to easily pass a needle and suture therethrough.

Referring now particularly to FIG. 1, the use of the marker/connector 10 in the RYGB procedure is illustrated. The patient's stomach 20 is completely divided into two unequal portions—a small upper pouch 22 and a large lower gastric pouch 24 (or excluded stomach). The upper pouch 22 typically measures less than about one ounce, preferably about one-half ounce, or 15 cc, while the larger lower pouch 24 remains generally intact and continues to secrete stomach juices that flow through the intestinal tract.

The small intestine 26 is severed at a location distal of the duodenum 28 or proximal of the jejunum (not shown). The severed end 30 of the small intestine then is brought from the lower abdomen, behind the colon and the bypassed stomach, and joined with the upper pouch 22 to form an end-to-end anastomosis 32 created through a half-inch opening, also called the stoma. This rerouted segment 34 of the small intestine is called the "Roux loop" and carries food from the upper pouch 22 to the remainder of the intestines where the food is digested. The severed end 36 of the segment of the duodenum 28 that is attached to the lower pouch 24 of the stomach 20 is connected to the Roux loop 34 by means of an anastomotic connection indicated at 38. The connection 38 is located approximately 100 cm from the stoma 32, and typically is made by using a stapling instrument.

A gastropexy is performed, whereby the excluded stomach 24 is connected to the abdominal wall 40 by means of the marker/connector 10. Sutures 42 are passed through the loops 14 and through the tissue of the adjacent pouch 24 and the abdominal wall 40. The marker/connector 10 thus serves as a fluoroscopic marker as well as a mechanical connector between the excluded stomach 24 and the abdominal wall 40. If it is necessary to insert an endoscope or a trochar into the excluded stomach 24, the endoscope or trochar can be inserted through the ring 12 which will serve as a target as well as a means for holding the excluded stomach 24 in place as the endoscope or trochar is inserted therethrough.

Figure 4:
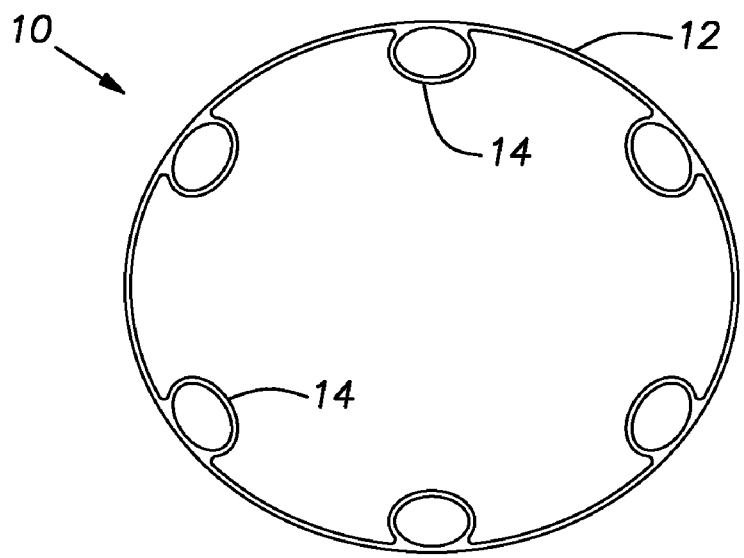
FIG. 4. is a top plan view of a surgical marker/connector according to the invention in which loops are disposed about the inner periphery of a ring.
Figure 5:
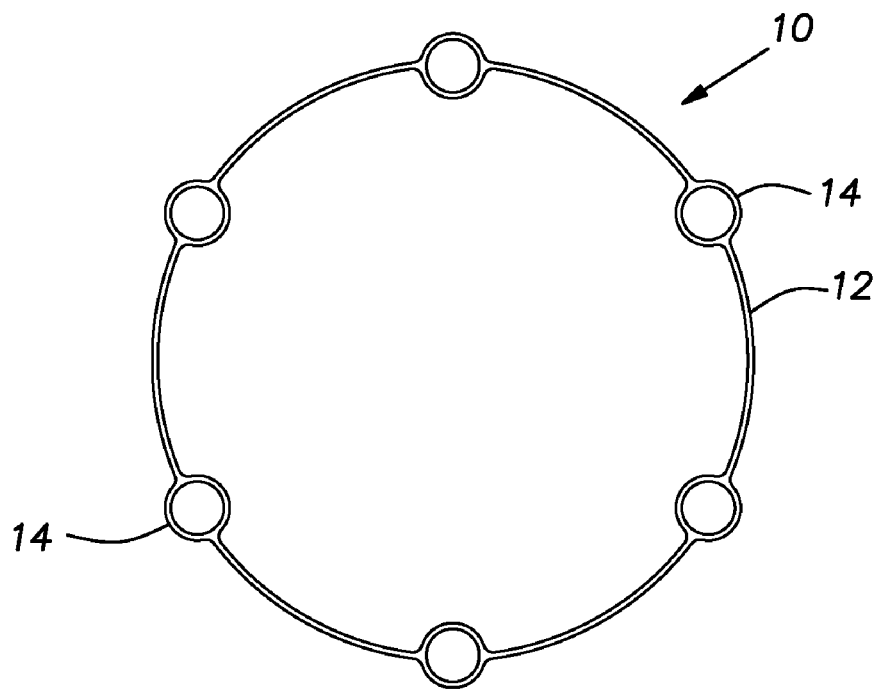
FIG. 5. is a top plan view of a surgical marker/connector according to the invention in which loops are incorporated as part of a ring.

As will be apparent from the foregoing description, the surgical marker/connector 10 according to the invention is easy to install. The marker/connector 10 avoids the use of undesirable hooks or barbs, while permitting the surgeon to securely attach the marker/connector to a desired portion of a patient's body. In those instances where the marker/connector 10 is used as a mechanical connector between adjacent portions of the patient's body, the connection is easy to make and is quite secure and strong. The ring 12 provides a target through which an endoscope or a trochar can be inserted, if necesssary Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. For example, and not by way of limitation, the ring 12 could be non-circular (see FIG. 4 where the ring 12 is slightly elliptical and the loops 14 could be shapes other than generally elliptical. (see FIG. 5, where the loops 14 are circular). By way of further example and not by way of limitation, some or all of the loops 14 could be disposed on the inner diameter of the ring 12 (see FIG. 4) or some or all of the loops 14 could be formed as part of the ring 12 itself.(see FIG. 5). It is intended that the patent shall cover, by suitable expression in the appended claims, whatever features of patentable novelty exist in the invention disclosed.

What is claimed is:

1. A surgical implant and marker/connector for installation in a patient, consisting of:
    a closed, thin ring of fixed dimensions lying substantially in a single plane and having an absence of hooks or barbs, the ring being made of a biocompatible material suitable for fluoroscopic marking and having a strength suitable for connecting tissue in the intestinal region of the patient;
    the ring having an inner diameter and an outer diameter, the inner diameter defining an opening of a size and shape suitable for being pierced by an endoscope or a trochar when the ring is installed in a patient;
    a plurality of suture attachments disposed equidistantly about the periphery of the ring and lying in the plane in which the ring lies, the suture attachments being disposed on the inner diameter of the ring, the outer diameter of the ring, forming a portion of the ring, or combinations thereof; and
    the suture attachments being in the form of small loops, each loop defining an opening of a size and shape through which a needle and suture can be passed, the area of each of the loops being substantially smaller than the area of the opening defined by the inner diameter of the ring.

2. The surgical implant and marker/connector of claim 1, wherein six suture attachments are provided.

3. The surgical implant and marker/connector of claim 1, wherein the area of the opening defined by the inner diameter of the ring is approximately 0.785 square inch and the area of the opening defined by each loop is approximately 0.00785 square inch.

4. The surgical implant and marker/connector of claim 1, wherein the ring and the loops have a thickness and a width, the thickness being approximately 0.0085 inch and the width being approximately 0.010 inch.

5. The surgical implant and marker/connector of claim 1, wherein the suture attachments are disposed only on the outer diameter of the ring.

6. The surgical implant and marker/connector of claim 1, wherein the ring is circular and the suture attachments are generally elliptical.

7. The surgical implant and marker/connector of claim 1, wherein the ring and the suture attachments are made of the same material.

8. The surgical implant and marker/connector of claim 1, wherein the ring and the suture attachments are made of a material selected from the group consisting of stainless steel and alloys thereof and titanium and alloys thereof.

9. The surgical implant and marker/connector of claim 1, wherein the ring and the suture attachments are made in a laser cutting or a stamping operation.

10. A surgical implant and marker/connector for installation in a patient, consisting of:
    a closed, thin ring of fixed dimensions lying substantially in a single plane and having an absence of hooks or barbs, the ring being made of a biocompatible material suitable for fluoroscopic marking and having a strength suitable for connecting tissue in the intestinal region of the patient;
    the ring having an inner diameter and an outer diameter, the inner diameter defining a generally circular opening having an area of approximately 0.785 square inch
    six suture attachments disposed equidistantly about the periphery of the ring and lying in the plane in which the ring lies, the suture attachments being disposed on the inner diameter of the ring, the outer diameter of the ring, forming a portion of the ring, or combinations thereof;
    the suture attachments being in the form of generally elliptical loops each defining an opening having an area of approximately 0.0785 square inch;
    the ring and the loops having a width and a thickness, the thickness being approximately 0.0085 inch and the width being approximately 0.010 inch; and
    the ring and the suture attachments being made of the same material, the material being selected from the group consisting of stainless steel and alloys thereof and titanium and alloys thereof.

11. The surgical implant and marker/connector of claim 10, wherein the suture attachments are disposed only on the outer diameter of the ring.

12. The surgical implant and marker/connector of claim 10, wherein the ring and the suture attachments are made in a laser cutting or a stamping operation.

* * * * *